United States Patent [19]
Koppikar

[11] Patent Number: 5,576,550
[45] Date of Patent: Nov. 19, 1996

[54] PHYTOLUMINOMETER

[75] Inventor: Mahesh M. Koppikar, Great Falls, Va.

[73] Assignee: Photonucleonics NDT, Inc., Lexington, Ky.

[21] Appl. No.: 376,000

[22] Filed: Jan. 20, 1995

Related U.S. Application Data

[62] Division of Ser. No. 140,278, Oct. 21, 1993, Pat. No. 5,406,089, which is a continuation of Ser. No. 421,835, Oct. 16, 1989, abandoned.

[51] Int. Cl.$^6$ .................................................. G01N 21/76
[52] U.S. Cl. ..................................... 250/459.1; 250/458.1
[58] Field of Search ........................... 250/459.1, 458.1, 250/461.1, 462.2, 361 C; 356/417, 317, 73

[56] References Cited

U.S. PATENT DOCUMENTS

| | | | |
|---|---|---|---|
| 4,142,101 | 2/1979 | Yin | 250/363 |
| 4,345,153 | 8/1982 | Yin | 250/369 |
| 4,791,300 | 12/1988 | Yin | 250/363 |
| 4,804,850 | 2/1989 | Norrish et al. | 250/459 |
| 4,948,975 | 8/1990 | Erwin et al. | 250/361 |

FOREIGN PATENT DOCUMENTS

WO87/06698 11/1987 WIPO.

OTHER PUBLICATIONS

Scientific paper entitled "Luminescence Analysis of Triplet States of Chlorophyll in Barley Leaves with Blocked Carotenoid Biosynthesis", A. A. Krasnovskii, Jr., Yu. V. Kovalev, et al., Biofizika 25(5), 1980.
Scientific paper entitled "Delayed Light Imaging for the Early Detection of Plant Stress", J. L. Ellenson & R. G. Amundson, Science 215:1104–1106, 1982.
Scientific paper entitled "Gas Exchange and Phytoluminography of Single Red Kidney Bean Leaves during Period of Induced Stomatal Oscillations", J. L. Elleson & R. M. Raba, Plant Physiol, 72:20–95, 1983.
Scientific paper by P. F. Daley, K. Raschke, J. T. Ball, J. A. Berry, Plant Physiol 90:1233–1238, 1989.
Information Sheet entitled "Look to COHU for Scientific Television".
Scientific paper entitled "Imaging by Delayed Light Emission (Phytoluminography) as a Method for Detecting Damage to the Photosynthetic System", L. O. Bjorn & A. S. Forsberg, Physiol Plant 47:215–222, 1979.
Scientific paper by E. Sundbom & L. O. Bjorn, Physiol Plant 40:39–41, 1977.
Scientific paper by R. Blaich, O. Bachmann, & I. Baumberger, Z Naturforsch Sect C Biosci 37 (5–6):452–457, 1982.
Title Page, Table of Contents, and selected portions from vol. 1, "Bioluminescence and Chemiluminescence: Instruments and Applications" (1985 CRC Press Inc.).
Copy of cover, title page, and selected pages from volume entitled "Luminescence Immunoassay and Molecular Applications" (1990 CRC Press Inc.).
Selected pages from Phillips Data Handbook (Book T13, 1986) from Image Intensifiers section pertaining to the XX1380 series.
Copy of brochure entitled "Litton Image Intensifiers", marked 10M–Jul. 1983 printed in the USA on last page.
Copy of brochure entitled "The Varo 25mm MCP Intensifier Model 3603".

Primary Examiner—Davis L. Willis
Assistant Examiner—Richard Hanig
Attorney, Agent, or Firm—Price, Heneveld, Cooper, DeWitt & Litton

[57] ABSTRACT

A hand-held, battery operated, single photon sensitivity phytoluminometer is claimed for rapid, simple nondestructive, noninvasive evaluation of photosynthetic topography in green leaves. All the steps for generating phytoluminescence are performed within a single, light tight enclosure. The sensitivity of the instrument is such that stress induced changes in photosynthesis can be detected seconds after occurrence. Thus phytoluminography is made an easily applied technique for practical use by all those concerned with plant life.

29 Claims, 6 Drawing Sheets

PHYTOLUMINOMETER

This is a divisional of copending application Ser. No. 8/140,278 filed on Oct. 21, 1993 now U.S. Pat. No. 5,406,089 which was a continuation of prior application Ser. No. 07/421,835 filed on Oct. 16, 1989 now abandoned.

BACKGROUND OF THE INVENTION

A bluish-green "Phosphorlicht" of living leaves was first observed by Carl von Szutz, an apothecary of Hungary, on the leaves of a garden plant, Phytolacca decanda (Linn), between 9 and 10 p.m. one evening in September, 1800. Szutz picked the leaves and the light continued to shine, sometimes yellowish-green, sometimes bluish, sometimes stronger, sometimes weaker, depending on whether the "Zug der Lade" was stronger or weaker. The phosphorescence lasted until after midnight and then disappeared. The light may have been an electrical phenomenon, although luminous fungi growing on living leaves is a second possibility (As quoted by E. Newton Harvey, in A History of Luminescence, The American Philosophical Society, Philadelphia, pp 486, 1957). Phytoluminescence was first described by Strehler and Arnold in 1951 (Strehler B. L. and Arnold W. 1951, Light production by green plants—J Gen Physiol 34:809–820). This extremely short lived light emission by living green plants is not visible to the unaided eye and not at all related to the observations of von Szutz. This emission of light is part of a photosynthetic reaction by excited states of chlorophyll and is dependent upon photosynthetic electron transport. A reversible injury causes an increase in light output probably by a decrease in photosynthesis and diversion of energy to phytoluminescence. Irreversible injury damages the entire photosynthetic mechanism and abolishes phytoluminescence. Phytoluminography is two dimensional imaging of phytoluminescence using high sensitivity light amplifiers. The technique was first described by Sundbom and Bjorn in 1977. Its use in early detection of plant stress has been frequently described in Soviet literature. A few selected references are listed:

1) E. Sundbom & L. O. Bjorn, Physiol Plant 40:39–41, 1977
2) L. O. Bjorn & A. S. Forsberg, IBID 47:215–222, 1979
3) A. A. Krasnovskii, Jr., Yu. V. Kovalev, et al., Biofizika 25(5), 1980
4) J. L. Ellenson & R. G. Amundson, Science 215:1104–1106, 1982
5) R. Blaich, O. Bachmann, & I. Baumberger, Z Naturforsch Sect C Biosci 37 (5–6):452–457, 1982
6) P. F. Daley, K. Raschke, J. T. Ball, & J. A. Berry, Plant Physiol 90:1233–1238, 1989

Phytoluminescence has been arbitrarily divided into chlorophyll fluorescence and delayed light emission by all the authors. We attribute this division to insensitive imaging techniques and can demonstrate these to be parts of a negative exponential luminescence decay. The prior art involves large, expensive apparatuses using conventional air coupled lenses, mechanical shutters, long optical paths and light sources that do not resemble sunlight. Since the apparatuses are not hand-held or battery operated, they are inconvenient for use outside the laboratory. This limits the use of this valuable technique and puts it beyond the reach of common farmers and horticulturists.

Schematics of typical apparatuses using the prior art are reproduced in FIGS. 1, 2, and 3 as published in references 1, and respectively.

SUMMARY OF THE INVENTION

The above and other disadvantages of prior art phytoluminography apparatuses are overcome by the present invention which provides a hand-held, battery operated, single photon sensitivity, large format device for quantitative imaging of phytoluminescence, referred to hereinafter as a "Phytoluminometer".

The present invention uses easily available electronic flashguns with xenon flashlamps to excite luminescence in leaves. Green leaves exposed to other types of light such as sunlight, fluorescent light, incandescent light will also exhibit this phenomenon. However, these sources of illumination are non-uniform in spatial intensity distribution, spectral emission pattern, non-reproducible and not suitable for quantitative work. The preferred configuration of the electronic flashgun would be in the form of a ring light for ease of incorporation into the phytoluminometer and uniform distribution of light when used with a diffuser. Other configurations would work for less critical applications. The light source can be used in a white light (polychromatic) mode. It can also be filtered with glass or gelatin filters for monochromatic mode. Xenon flashlamp sources may be operated at varying repetition rates for luminescence lifetime studies. Planar electroluminescent lamps are suitable for less intense excitation. Solid state laser diode sources can be used after beam expansion and can be pulsed. Two dimensional arrays of light emitting diodes (LEDs) can be used but provide nonuniform illumination.

The leaf surface is viewed by the light amplifier assembly without delay after luminous excitation with the source of excitation switched off. The leaf surface is placed or held directly against the planar input surface of a fused, coherent, rigid, fiberoptic light pipe, taper or flexible fiberoptic bundle. Gradient index (GRIN) self-focussing fibers may be used in the fiberoptics. A fiberoptic taper allows minification or magnification depending upon the application. Conventional air coupled lenses may be used if provided with plano concave fiberoptic faceplates to optimize coupling between the leaf and the light amplifier. Projection of the image of the leaf using standard focal length lenses is not acceptable because of severe transmission losses. When air coupled, multi-element, glass lenses are used the surface coupled to the light amplifier should be of a plano type again to reduce coupling losses.

Reflection losses caused within the coupling of polished planar surfaces are reduced by the use of optical greases such as Dow Corning Silicon Grease #Q2-3067 optimized for refractive indices of the glasses.

The light amplification can be performed with first, second, or third generation image intensifiers of the types commonly used in night vision devices. Second generation image intensifiers are preferred because of optimal spectral match between the phytoluminescent emission and the photocathode spectral response. Proximity focused, electrostatic inverter, gated or nongated image intensifiers with one or more microchannel plates may be used. Multistage, low noise amplification with luminous gains greater than $10^8$ is necessary for imaging the entire luminescence decay. This necessitates cascading at least two second generation image intensifiers. Hybrid types with second generation intensifier at the input end and first generation at the output end can be used but are currently twice as expensive. All of the above image intensifiers can be procured with self contained battery operated power supplies and automatic bright source protection and can be gated. All of them are available with plano fiberoptic input and output faceplates. This facilitates ease of coupling to imaging optics and to each other. The entire assembly is encased in a light tight aluminum or plastic housing. The material of the enclosure is not critical as long as phosphorescent or fluorescent materials are excluded. The batteries for operating the flashgun, image intensifiers as well as the variable gain controls, switches are external to the light tight enclosure. The intensified image may be viewed in subdued light, recorded with conventional 35 mm, Polaroid, still or movie film, video, analog or digital cameras. Analog images may be digitized for image storage, processing, analyses, transmission by use of commercially available software and hardware. The intensified image may be quantified in its entirety or fraction thereof using optical to electrical probes in conjunction with oscilloscopes or photometers.

DETAILED DESCRIPTION OF THE PREFERRED EMBODIMENT

The present invention is a process and apparatus for obtaining quantitative images of luminescence arising from plant leaves and other surfaces excited by an external source of light. The luminescent light distribution represents active sites of photosynthesis. Perturbation of photosynthesis caused by darkness, high concentrations or lack of $CO_2$, lack of $O_2$, extremes of temperatures, noxious gases, chemicals, bacterial, viral, and fungal infections, can be rapidly and easily demonstrated using this invention. The perturbed area will manifest itself as brighter than non-perturbed area if recoverable, and darker if irreversibly damaged. These changes are visible with the instrument described herein seconds after the damage and days or weeks before the damage is visible to the unaided eye. Consequently, this invention helps in very early detection of plant stress and prediction of recovery. Since the apparatus is small, portable, low cost, sensitive, easy to use, it is useful to farmers, plant nurseries, plant breeders and others involved in plant research. Herbicide and pesticide research as well as ecological and pollution research would also benefit from use of the instrument. Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1B:
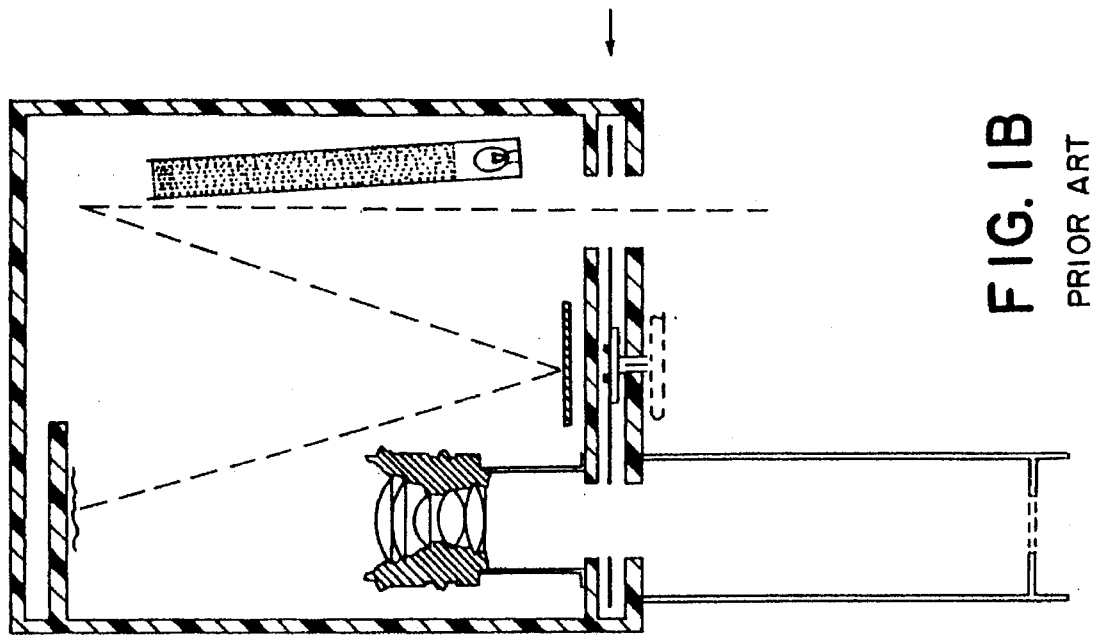
FIG. 1. is a schematic of one type of phytoluminography apparatus using prior art.
Figure 1A:
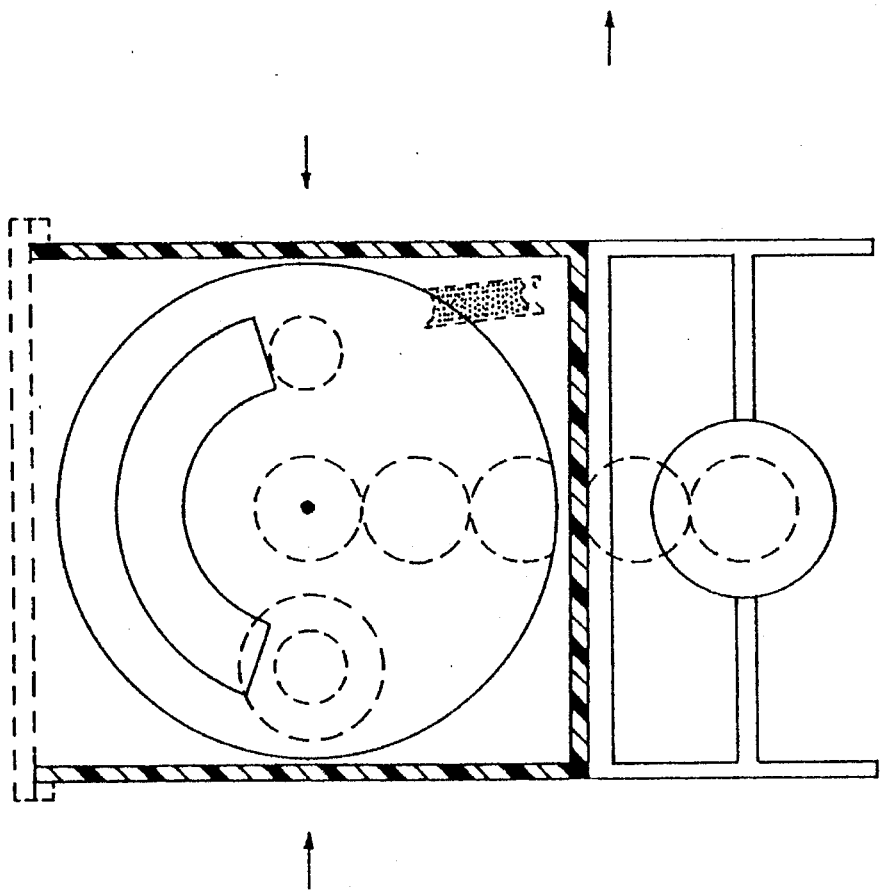
Figure 2B:
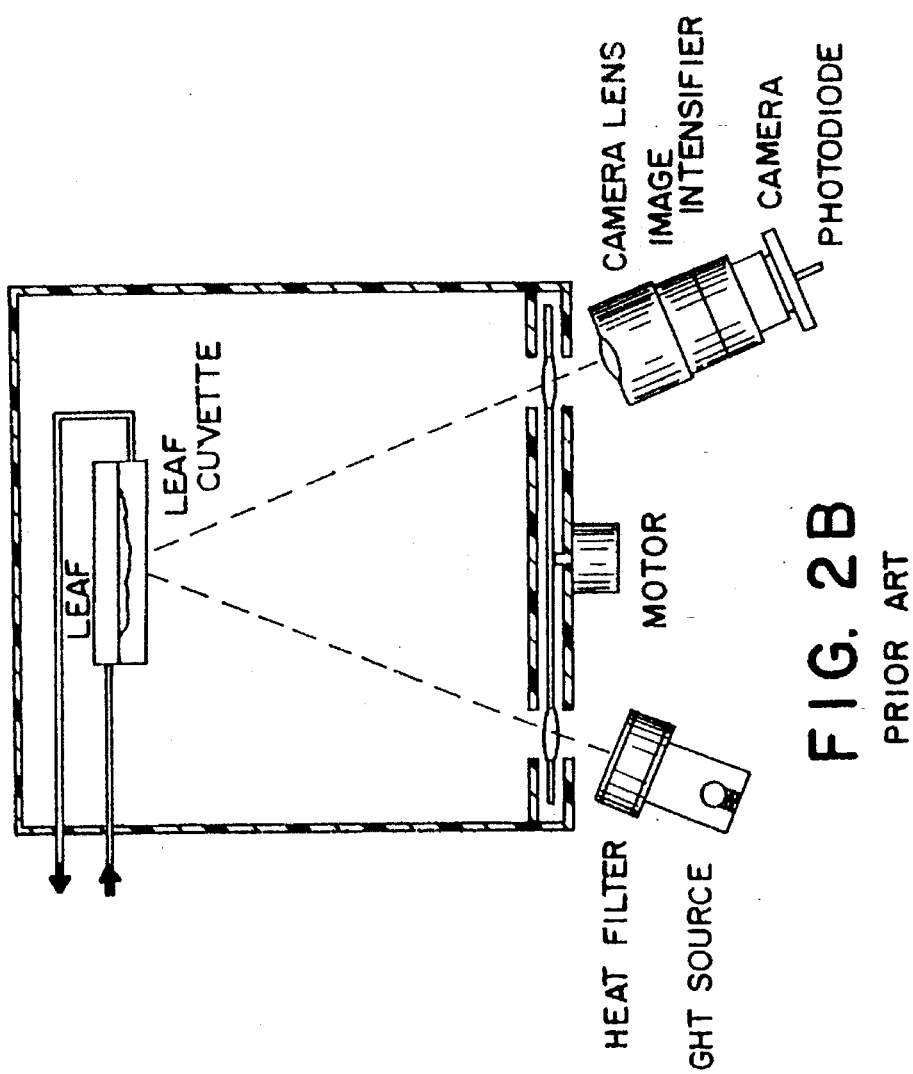
FIG. 2. is a schematic of a second type of phytoluminography apparatus using prior art.
Figure 2A:
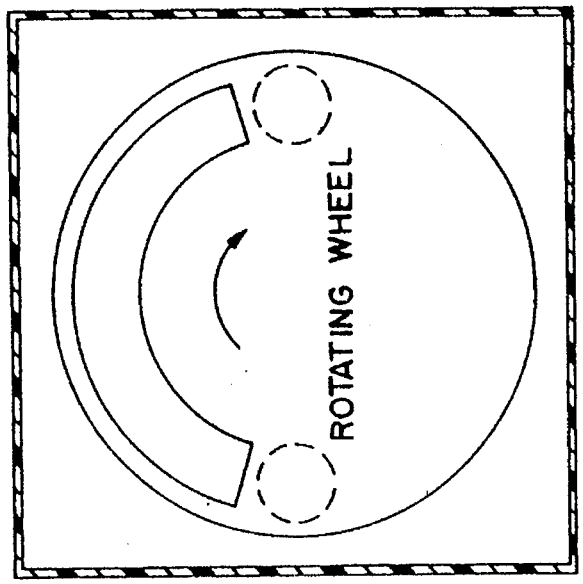
Figure 3:
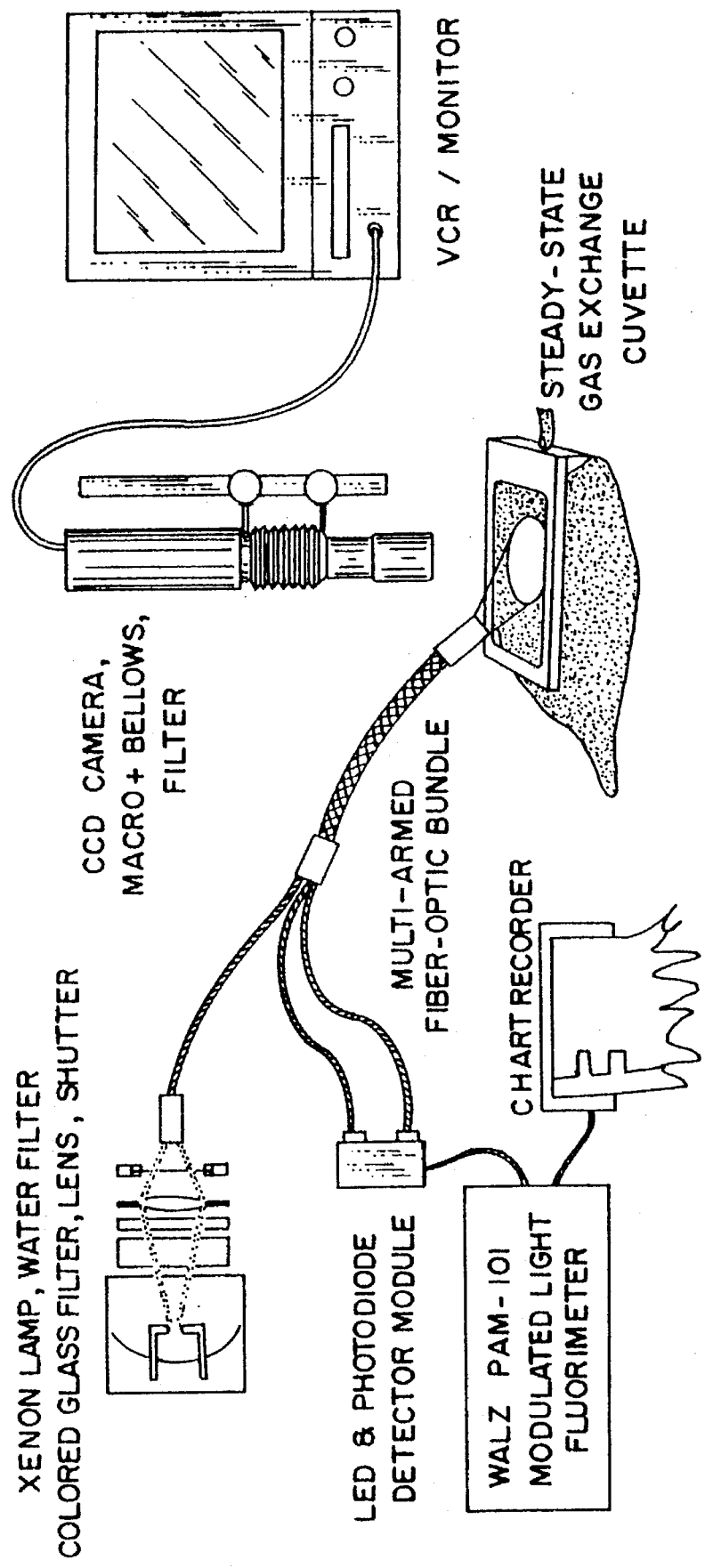
FIG. 3. is a schematic of a third type of phytoluminography apparatus using prior art.

Referring to FIGS. 1, 2, and 3, it will be apparent to those skilled in the art that most of the luminescent photon flux generated within the leaf surface is lost during transmission to the front surface of the air-coupled, multi-element imaging lenses. This reduces the sensitivity of the apparatus, creates multiple optical interfaces which are subject to moisture condensation, contamination, misalignment by shocks or vibration and need to be focussed. The mechanical shutters are too slow to respond to rapid luminescent changes. The illuminating systems have similar drawbacks of long distances, use of reflecting mirrors, and lamps not resembling solar spectral output. The bulky nature of the apparatus is immediately apparent. The use of only one stage of light amplification further contributes to the decreased sensitivity of the technique. Thus the use of the apparatus is limited to the laboratory.

Figure 4:
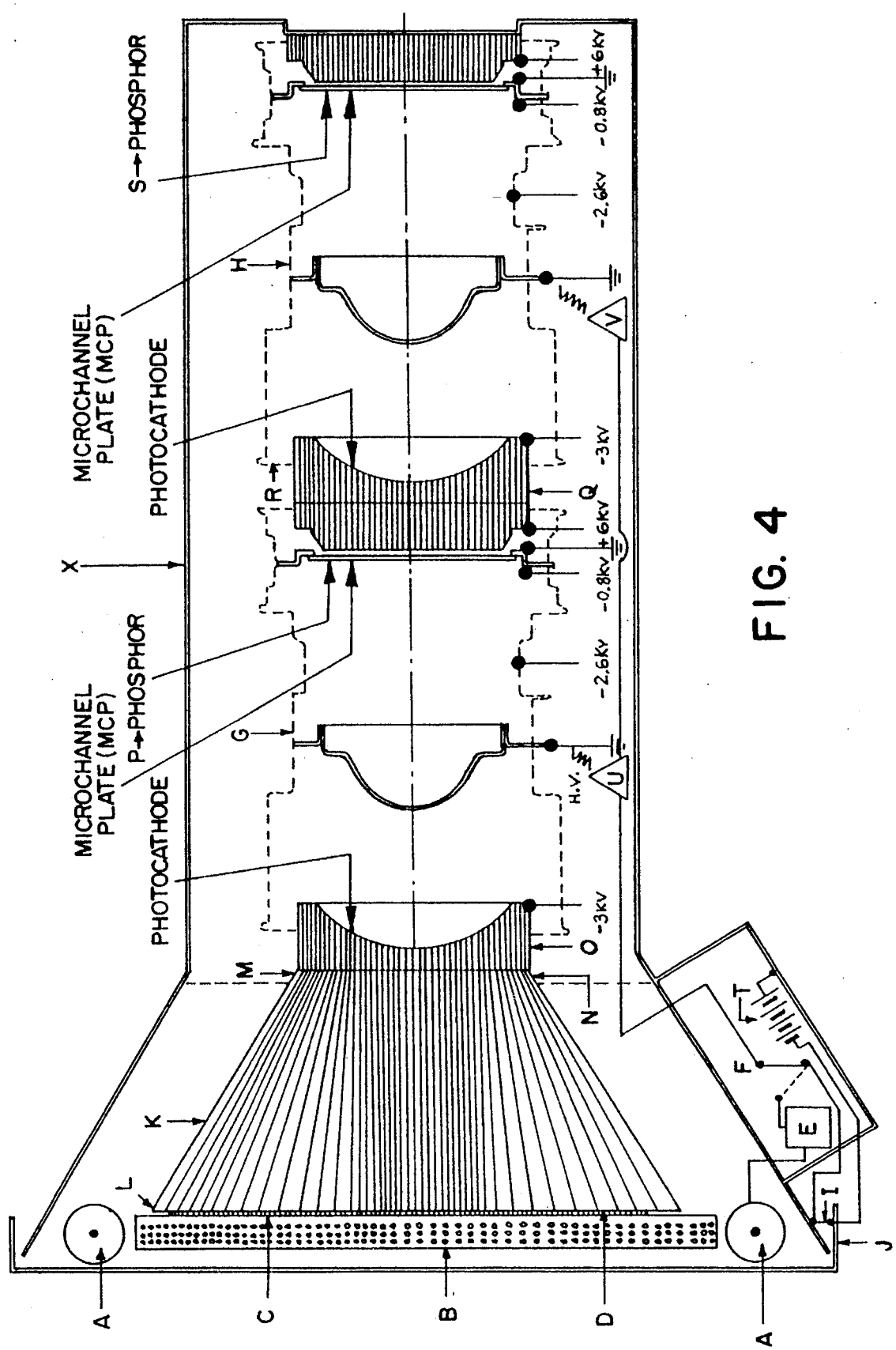
FIG. 4. demonstrates a schematic of the phytoluminometer using the current invention.
Figure 5:
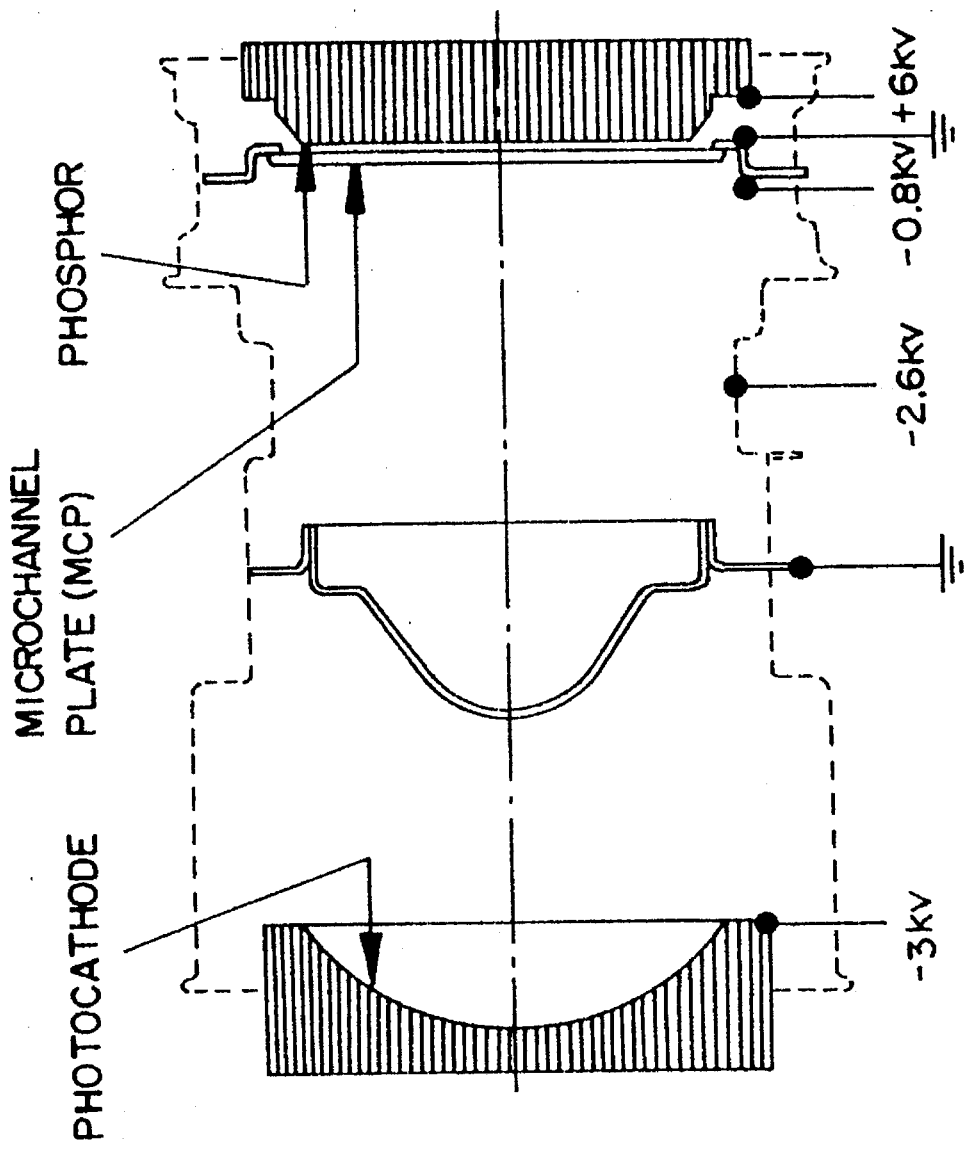
FIG. 5. represents a "second generation" image intensifier comprising multi-alkali photocathode, an electrostatic focussing system, a microchannel plate (MCP) as electron multiplier and a luminescent screen positioned immediately behind the MCP. A high voltage power supply operating from low voltage batteries is included in the encapsulation.
Figure 6B:
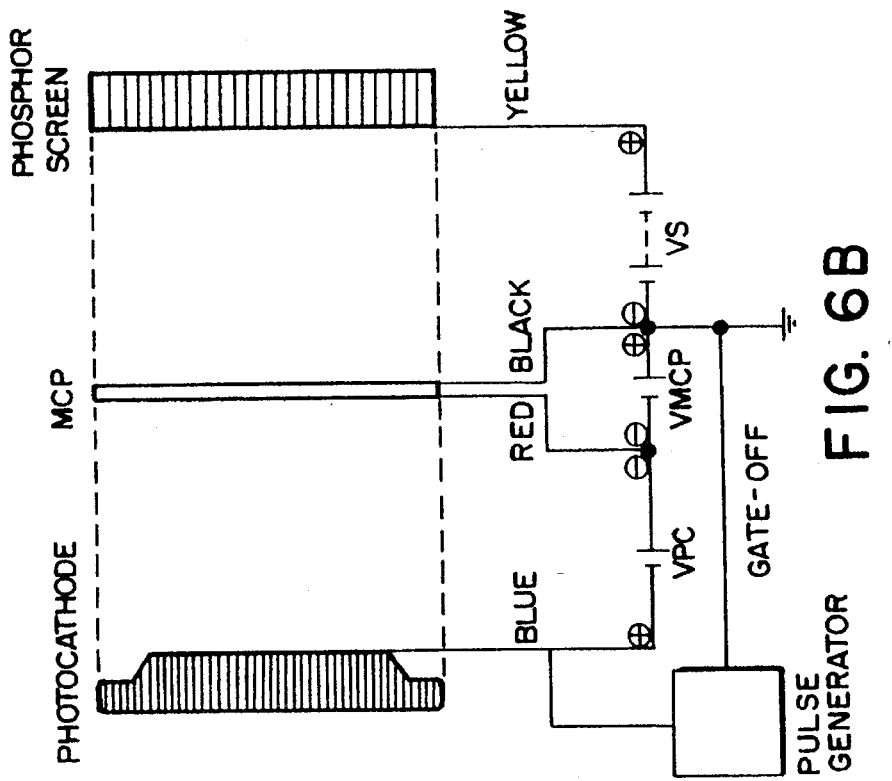
FIG. 6. represents a proximity focussed gated image intensifier with MCP and a gating power supply. This enables the tube to be switched within 5 nanoseconds for rapid electronic shuttering during luminescence lifetime studies.
Figure 6A:
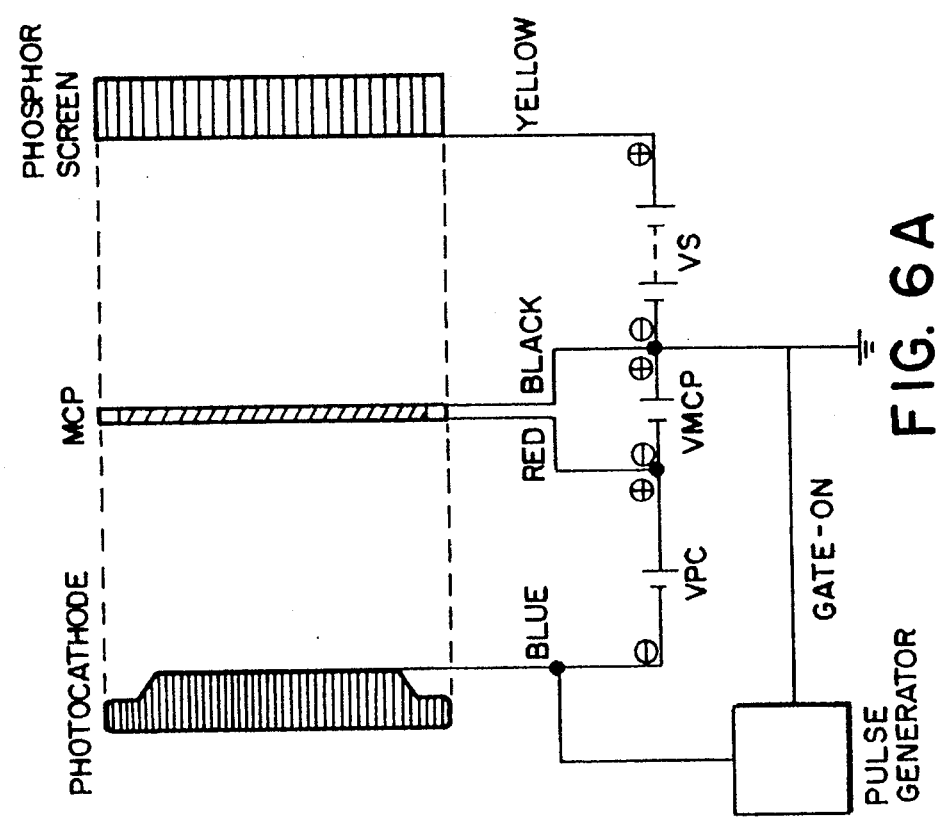

FIG. 4 refers to the schematic of the present invention. The excitation source A for illuminating the leaf is shown as an electronic flashgun with the xenon filled tube in a ring form. The light from the ring flash is diffused by a Lucite disc B within the ring. The Lucite disc B also serves as a support for the leaf D to be studied. Narrow or wide band, glass or gelatin filter C may be interposed between the Lucite support and the leaf D for monochromatic excitation. The power source E for the ring flash A is battery operated and external to the assembly X. The mechanical or electronic switch F allows either the excitation source A or the light amplifier G and H to be operational thus preventing damage to the light amplifiers by inadvertent exposure to high intensity light. A micro-switch I in the front removable cap J housing the ring flash A, diffusing disc B, leaf D switches off the light intensifiers when the cap J is removed thus protecting the amplifiers from ambient light. The imaging optic K is a fiberoptic taper with planar large and small surfaces. In operation leaf D on support B is directly in contact with the front surface L of the taper K. The rear surface M of the taper is coupled to the front fiberoptic faceplate N of the first stage image intensifier O. The rear fiberoptic output phosphor P of the first stage image intensifier is coupled directly to the front fiberoptic faceplate Q of the second stage image intensifier R. The output phosphor S of the second stage intensifier R is not covered by the enclosure X and thus is visible to the eye. The output phosphor S can also be coupled to optical cameras. The power source for the image intensifiers is provided by the batteries T providing power to E as well.

All fiberoptic coupling surfaces should use a thin layer of Dow Corning Q2-3067 optical couplant taking great care to exclude air bubbles. This reduces reflection losses, maintains tight but removable contact between surfaces and is immune to humidity, temperature changes.

The image intensifier tubes used in this apparatus should have the highest available photocathode sensitivity, in the spectral emission band of phytoluminescence, best signal to noise ration, lowest equivalent background illumination (EBI), minimum number of blemishes, hot spots. Standard military grade image intensifiers used in night vision devices are not preferred. Astronomical grade tubes should be specified. Second generation tubes with high output type (HOT) MCPs are preferred. When research applications with luminescence lifetime detection are involved fast output phosphors such as P-11 should be specified for the image intensifiers. Multi-colored current sensitive phosphors such as PT-452 will provide good contrast discrimination without computer enhancement.

Proximity focus, gated wafer tubes may be used in the first or second stage for rapid electronic switching of light amplification and for protection during strobing. It is preferable to operate photocathode and output phosphor surfaces close to ground potential to eliminate arcing, ion flashes, leakages between opposing coupled surfaces. A thin conductive coating with optical transparency such as tin oxide (NESA) should be applied to output fiberoptics for grounding it.

The entire assembly is encased in a light tight plastic or metal enclosure with care taken to exclude all fluorescent or phosphorescent materials such as paints, adhesives, detergents, optical brighteners. The low voltage battery power supply and adjustable gain controls for the image intensifiers are located outside the light enclosure but are connected to it by a cable or mounted on it. The switching functions and gain control can be controlled by a computer for nonportable applications. The manual gain controls should preferably be ten turn, wire wound potentiometers with turns indicator dial for precise setting and resetting of gain.

If an analog video camera is used for recording, then the video signal may be digitized for image acquisition, storage, analyses, quantitation, and enhancement. The hardware and software for accomplishing these functions are widely available commercially and need not be described here.

I claim:

1. A portable phytoluminometer, for producing a visible image of at least a portion of a green leaf including a two-dimensional distribution of active photosynthetic sites by using the photoluminescence of such sites as the illumination reproduced in the image, comprising:

means for having at least said portion of said leaf in direct optical coupling with an optical input surface;

means for detecting said photoluminescence at said sites in said distribution; and means for producing a visible image of said distribution of sites by using said detected photoluminescence; said means together comprising a device of sufficiently small size and low weight as to be readily transportable and operated by a single individual and including a lightweight self-contained power supply carried therewith, said means further comprising at least one electron-amplifying image-intensifier powered by said self-contained supply.

2. A phytoluminometer according to claim 1 in which said electron-amplifying image intensifier comprises at least two cascaded stages of image intensification.

3. A photoluminometer according to claim 2 including means for switching at least one of said two cascaded stages.

4. A phytoluminometer according to claim 2, wherein said stages generally comprise image intensifiers selected from the group consisting of first, second, or third generation devices.

5. A phytoluminometer according to claim 4, including an optical output and means for direct-coupling said image intensifier stages to said input and output.

6. A phytoluminometer according to claim 5, wherein the first of said two stages comprises a second-generation intensifier.

7. A phytoluminometer according to claim 6, wherein the second of said stages comprises of a first-generation intensifier.

8. A phytoluminometer according to claim 6, wherein the second of said states comprises of a second-generation intensifier.

9. A portable phytoluminometer, for producing a visible image of at least a portion of a green leaf including a two-dimensional distribution of active photosynthetic sites by using the luminescence of such sites as the illumination reproduced in the image, comprising:

means for having at least said portion of said leaf in direct optical coupling with an optical input surface;

an integrally associated light source for exciting said leaf to a state of luminescence;

means for detecting the luminescence at said sites in said distribution;

means for producing a visible image of said distribution of sites by using said detected luminescence;

said light source being attached to and carried with said means for producing a visible image of photosynthetic sites;

said means together comprising a device of sufficiently small size and low weight as to be readily transportable and operated by a single individual and including a lightweight self-contained power supply carried therewith; and said light source being electrically coupled to said power supply for operating excitation.

10. A portable phytoluminometer according to claim 9, wherein said light source comprises an annular device which generally encircles said leaf when it is coupled with said optical input surface.

11. A portable phytoluminometer according to claim 10, and further including a light-diffuser element disposed generally radially inward of said annular light source.

12. A portable phytoluminometer according to claim 9, wherein said means for producing a visible image has an optical input element comprising an optically transmissive end surface for receiving said leaf in close physical association.

13. A method of imaging luminescent samples, comprising the steps:

positioning a selected luminescent sample in direct contact with an optical input surface and directly optically coupling said input surface to at least a first stage of image intensification;

converting luminescent light energy from said sample into a corresponding electron flow and amplifying said electron flow in at least said first stage of image intensification;

converting the amplified electron flow into light energy of substantially greater magnitude than that initially obtained from said sample by coupling the output of said image intensification stage to a conversion device;

displaying the resulting light energy from said conversion device as a visible image on an output member which is directly coupled optically to said conversion device; and using an active-type image-intensifier as said first stage and selecting the photocathode spectral response of said active-type image-intensifier to match the spectral emission of said luminescent sample.

14. The method as set forth in claim 13, including the step of optically exciting said sample prior to said step of converting luminescent light.

15. The method as set forth in claim 14, wherein said step of optically exciting said sample is carried out by use of a ring-type electronic flashgun.

16. The method as set forth in claim 15, including the step of filtering the light from said flashgun as part of said step of optical excitation.

17. The method as set forth in claim 13, wherein said step of amplifying said electron flow is carried out by using active-type image-intensification means having an overall luminous gain of at least $10^8$.

18. The method as set forth in claim 17, wherein said step of amplifying is carried out by using at least two stages of active image intensifiers which are cascaded together for operation.

19. The method as set forth in claim 13, including the steps of using an end surface of a light-transmissive solid-state member as said optical input surface, using a solid-state-type conversion device, and directly optically coupling said light-transmissive member, said stage of image-intensification and said solid-state conversion device by using an optical couplant gel on the contiguous surfaces of each.

20. A method of imaging luminescent samples, comprising the steps:

positioning a selected luminescent sample in direct contact with an optical input surface and directly optically coupling said input surface to at least a first stage of image intensification;

converting luminescent light energy from said sample into a corresponding electron flow and amplifying said electron flow in at least said first stage of image intensification;

converting the amplified electron flow into light energy of substantially greater magnitude than that initially obtained from said sample by coupling the output of said image intensification stage to a conversion device;

displaying the resulting light energy from said conversion device as a visible image on an output member which is directly coupled optically to said conversion device; and using a second-generation image-intensifier element having a high-output type ("H.O.T.") microchannel plate electron multiplier in said step of image intensification.

21. a method of imaging luminescent samples, comprising the steps:

positioning a selected luminescent sample in direct contact with an optical input surface and directly optically coupling said input surface to at least a first stage of image intensification;

converting luminescent light energy from said sample into a corresponding electron flow and amplifying said electron flow in at least said first stage of image intensification;

converting the amplified electron flow into light energy of substantially greater magnitude than that initially obtained from said sample by coupling the output of said image intensification stage to a conversion device;

displaying the resulting light energy from said conversion device as a visible image on an output member which is directly coupled optically to said conversion device; and using a fast output phosphor such as that known as P-11 for said solid-state conversion device.

22. a method of imaging luminescent samples, comprising the steps:

positioning a selected luminescent sample in direct contact with an optical input surface and directly optically coupling said input surface to at least a first stage of image intensification;

converting luminescent light energy from said sample into a corresponding electron flow and amplifying said electron flow in at least said first stage of image intensification;

converting the amplified electron flow into light energy of substantially greater magnitude than that initially obtained from said sample by coupling the output of said image intensification stage to a conversion device;

displaying the resulting light energy from said conversion device as a visible image on an output member which is directly coupled optically to said conversion device; and using a multi-colored current-sensitive phosphor such as PT-452 for said solid-state conversion device to achieve enhanced contrast discrimination in said visible image displayed on said member.

23. a method of imaging luminescent samples, comprising the steps:

positioning a selected luminescent sample in direct contact with an optical input surface and directly optically coupling said input surface to at least a first stage of image intensification;

converting luminescent light energy from said sample into a corresponding electron flow and amplifying said electron flow in at least said first stage of image intensification;

converting the amplified electron flow into light energy of substantially greater magnitude than that initially obtained from said sample by coupling the output of said image intensification stage to a conversion device;

displaying the resulting light energy from said conversion device as a visible image on an output member which is directly coupled optically to said conversion device; and using a first stage of image intensification which includes at least one photocathode and a conversion device which includes an output phosphor, and operating said photocathode and output phosphor at an electrical potential which is close to ground potential to reduce adverse effects such as arcing, ion flashes and leakage current.

24. A method of imaging luminescent samples, comprising the steps:

positioning a selected luminescent sample in direct contact with an optical input surface and directly optically coupling said input surface to at least a first stage of image intensification;

converting luminescent light energy from said sample into a corresponding electron flow and amplifying said electron flow in at least said first stage of image intensification;

converting the amplified electron flow into light energy of substantially greater magnitude than that initially obtained from said sample by coupling the output of said image intensification stage to a conversion device;

displaying the resulting light energy from said conversion device as a visible image on an output member which is directly coupled optically to said conversion device; and using an output member comprising a fiberoptic bundle having optically transmissive end surfaces, coating at least one such end surface with a thin layer of electrically conductive and optically transmissive material, and using said coating to electrically ground said surface.

25. A small, lightweight, manually-transportable, real-time imaging device of high sensitivity, comprising in combination:

solid-state optical input means comprising coherent self-focussing optical fibers having a light-transmissible surface adapted for direct optical coupling with an examination subject;

at least one stage of electron-multiplication image intensification; means for establishing direct optical coupling between said input means and said at least one stage of image intensification; and solid-state output means directly optically coupled to the last of said at least one stage of image intensification, for visually displaying a real-time image of said examination subject;

said fiberoptic bundle including an optical taper for effecting image minification or magnification; and said optical taper comprising at least one lens element directly optically coupled between a pair of adjacent fiberoptic faceplates formed serially in said bundle.

26. The imaging device of claim 25, wherein said lens element and said fiberoptic faceplates are coupled by an interposed layer of optical grease.

27. The imaging device of claim 25, wherein said lens element includes a plano surface on its side facing said first stage of image intensification.

28. The imaging device of claim 25, and further including a generally tubular light-tight housing laterally enclosing and providing means for carrying said stages of image intensification, said means for establishing optical coupling, and at least portions of said solid-state optical input means and output means.

29. The imaging device of claim 25, including means for direct-coupling all of the optical stages from said input means to said output means, said means including a layer of optical-grade gel as a couplant between adjacent directly-coupled optical surfaces, whereby said imaging device possesses single-photon sensitivity.

* * * * *